United States Patent
Harima et al.

(10) Patent No.: US 7,072,791 B2
(45) Date of Patent: Jul. 4, 2006

(54) PEDOMETER FOR USE WITH PREGNANT WOMAN

(75) Inventors: Shinichi Harima, Fujimi (JP); Noriko Inoue, Akita-ken (JP); Kazumi Sano, Tokorozama (JP); Yuriko Nakayama, Tokyo (JP)

(73) Assignee: Tanita Corporation, Tokyo (JP)

( * ) Notice: Subject to any disclaimer, the term of this patent is extended or adjusted under 35 U.S.C. 154(b) by 41 days.

(21) Appl. No.: 10/874,376

(22) Filed: Jun. 24, 2004

(65) Prior Publication Data

US 2005/0020888 A1    Jan. 27, 2005

(30) Foreign Application Priority Data

Jun. 24, 2003  (JP)  .............................. 2003-179338

(51) Int. Cl.
*G01C 22/00*  (2006.01)
(52) U.S. Cl. .................................................... 702/160
(58) Field of Classification Search ................ 702/86, 702/97, 158, 160, 161
See application file for complete search history.

(56) References Cited

U.S. PATENT DOCUMENTS

| | | | |
|---|---|---|---|
| 4,560,861 A | * | 12/1985 | Kato et al. ................... 235/105 |
| 4,951,197 A | | 8/1990 | Mellinger |
| 2002/0133378 A1 | | 9/2002 | Mault et al. |
| 2005/0043647 A1 | * | 2/2005 | Kodama ..................... 600/551 |

FOREIGN PATENT DOCUMENTS

| JP | 8-38462 | 2/1996 |
|---|---|---|
| JP | 2002-190007 A | 7/2002 |

OTHER PUBLICATIONS

English Translation of JP 08-38462, Feb. 13, 1996.*

* cited by examiner

*Primary Examiner*—Michael Nghiem
(74) *Attorney, Agent, or Firm*—McDermott Will & Emery LLP (57) ABSTRACT

A pedometer is provided for use by a pregnant woman. Embodiments include a pedometer having a number-of-activity step acquisition unit that acquires the number of activity steps taken by the pregnant woman, an activity energy consumption calculation unit that calculates activity energy consumption caused by the number of activity steps, and a proper energy consumption storage unit that stores proper energy consumption for the pregnant woman. A comparison and assessment unit compares the activity energy consumption with the corresponding proper energy consumption and assesses the activity energy consumption of the pregnant woman. A comparison and assessment result output unit outputs the result of the comparison and assessment.

19 Claims, 9 Drawing Sheets

PROPER ENERGY CONSUMPTION SELECTION TABLE FOR THE CASE OF "BMI" <17

| | | TERM ELAPSED AFTER PREGNANCY / INTENSITY IN ACTIVITY IN LIFE | 1ST WEEK AFTER PREGNANCY | ... | 15TH WEEK AFTER PREGNANCY | ... | 30TH WEEK AFTER PREGNANCY | ... | LACTATION (AFTER DELIVERY) |
|---|---|---|---|---|---|---|---|---|---|
| BMI<17 | | LOW | 150 | ... | 250 | ... | 350 | ... | 750 |
| | | SLIGHTLY LOWER | 200 | ... | 300 | ... | 400 | ... | 800 |
| | | MODERATE | 250 | ... | 350 | ... | 450 | ... | 850 |
| | | HIGH | 300 | ... | 400 | ... | 500 | ... | 900 |

PROPER ENERGY CONSUMPTION (kcal/day)

FIG.5

PROPER ENERGY CONSUMPTION SELECTION TABLE FOR THE CASE OF 17≦"BMI"<24

| INTENSITY IN ACTIVITY IN LIFE \ TERM ELAPSED AFTER PREGNANCY | 1ST WEEK AFTER PREGNANCY | ... | 15TH WEEK AFTER PREGNANCY | ... | 30TH WEEK AFTER PREGNANCY | ... | LACTATION (AFTER DELIVERY) |
|---|---|---|---|---|---|---|---|
| LOW | 200 | ... | 300 | ... | 400 | ... | 800 |
| SLIGHTLY LOWER | 250 | ... | 350 | ... | 450 | ... | 850 |
| MODERATE | 300 | ... | 400 | ... | 500 | ... | 900 |
| HIGH | 350 | ... | 450 | ... | 550 | ... | 950 |

17≦BMI<24

PROPER ENERGY CONSUMPTION (kcal/day)

FIG.6

PROPER ENERGY CONSUMPTION SELECTION TABLE FOR THE CASE OF 24≦"BMI"

| | TERM ELAPSED AFTER PREGNANCY / INTENSITY IN ACTIVITY IN LIFE | 1ST WEEK AFTER PREGNANCY | ... | 15TH WEEK AFTER PREGNANCY | ... | 30TH WEEK AFTER PREGNANCY | ... | LACTATION (AFTER DELIVERY) |
|---|---|---|---|---|---|---|---|---|
| 24≦BMI | LOW | 250 | ... | 350 | ... | 450 | ... | 850 |
| | SLIGHTLY LOWER | 300 | ... | 400 | ... | 500 | ... | 900 |
| | MODERATE | 350 | ... | 450 | ... | 550 | ... | 950 |
| | HIGH | 400 | ... | 500 | ... | 600 | ... | 1000 |

PROPER ENERGY CONSUMPTION (kcal/day)

FIG.7

ADVICE SELECTION TABLE

| ADVICE DECISION CRITERION | ADVICE |
|---|---|
| NUMBER OF ACTIVITY STEPS < 50% OF PROPER NUMBER OF STEPS | WALK MORE AND MORE, TODAY! |
| 50% OF PROPER NUMBER OF STEPS ≦ NUMBER OF ACTIVITY STEPS < 70% OF PROPER NUMBER OF STEPS | WALK MORE, TODAY! |
| 70% OF PROPER NUMBER OF STEPS ≦ NUMBER OF ACTIVITY STEPS < 90% OF PROPER NUMBER OF STEPS | WALK SLIGHTLY MORE, TODAY! |
| 90% OF PROPER NUMBER OF STEPS ≦ NUMBER OF ACTIVITY STEPS < 110% OF PROPER NUMBER OF STEPS | YOU ARE SUFFICIENT, TODAY. WALK TOMORROW AT THE SAME PACE! |
| 110% OF PROPER NUMBER OF STEPS ≦ NUMBER OF ACTIVITY STEPS < 130% OF PROPER NUMBER OF STEPS | STOP WALKING SOON, TODAY! |
| 130% OF PROPER NUMBER OF STEPS ≦ NUMBER OF ACTIVITY STEPS | YOU SATISFACTORY WALKED, TODAY. STOP WALKING RIGHT AWAY! WALK TOMORROW UP TO PROPER NUMBER OF STEPS! |

PEDOMETER FOR USE WITH PREGNANT WOMAN

BACKGROUND OF THE INVENTION

1. Field of the Invention

The present invention relates to a pedometer, and more particularly, to a pedometer for use with a pregnant woman.

2. Prior Art

A pedometer is well known as one of the health care means. Many types of pedometers have been available in the market from the classical one in which the number of steps that a user actually walked is simply displayed to the new one that has recently been developed in which, in addition to the number of steps, an additional information necessary for health care including e.g. calorie value and body fat mass consumed by walking is displayed. One example of the pedometer in the later case is disclosed in Japanese Patent Laid-Open Nos. 8-38462 and 2002-190007. The device as disclosed therein is configured to measure the number of steps and to calculate and display calorie consumption or fat mass consumption in order to know how much body fat is burned due to the walking activity (or the number of steps).

The patent documents associated with the present invention are as follows:

Patent Document 1: Japanese Patent Laid-Open No. 8-38462; and

Patent Document 2: Japanese Patent Laid-Open No. 2002-190007.

However, the pedometer having capability of displaying health care information in addition to the number of steps, as described above, is generally designed for use with normal persons including male and female people. On the other hand, for pregnant women who are under the specific circumstances, control of calorie intake and calorie consumption has been conducted in view of weight increase (or body fat deposition) during pregnant period and of health care. Accordingly, it is highly desirable for those pregnant women to have some device that is capable of simply controlling calorie intake or calorie consumption during the pregnant period and the predetermined term after delivery. Unfortunately, due to the fact that the prior art pedometer is designed for use with the common people in normal condition, as described above, then it is not effective for pregnant women to use it without any modification for the purpose of health care during the pregnant period and the predetermined term after delivery. Rather, there may possibility of adverse effect of the prior art pedometer on the pregnant women.

In view of the above an object of the present invention is to provide an improved pedometer for use with pregnant women to conduct health care during pregnant period and the predetermined interval after delivery.

SUMMARY OF THE INVENTION

To attain such object the present invention provides a pedometer for use with a pregnant woman, comprising: a fat deposition related factor acquisition unit; a term-after-pregnancy acquisition unit; a number-of-activity step acquisition unit; an activity energy consumption calculation unit; a proper energy consumption storage unit; a comparison and assessment unit; and a comparison and assessment result output unit, wherein said fat deposition related factor acquisition unit acquires a factor related to fat deposition of the pregnant woman, said term-after-pregnancy acquisition unit acquires term that has elapsed after pregnancy, said number-of-activity step acquisition unit acquires the number of activity steps taken by the pregnant woman, said activity energy consumption calculation unit calculates activity energy consumption caused by said number of activity steps acquired, said proper energy consumption storage unit stores proper energy consumption for the pregnant woman, said comparison and assessment unit compares the activity energy consumption calculated by said activity energy consumption calculation unit with the corresponding proper energy consumption stored in said proper energy consumption storage unit for assessing the activity energy consumption, and said comparison and assessment result output unit outputs the result of comparison and assessment for the activity energy consumption made by said comparison and assessment unit.

According to one embodiment of the present invention said proper energy consumption storage unit stores the proper energy consumption in the form of proper energy consumption selection table in which the factor related to fat deposition and the term elapsed after pregnancy are listed in corresponding relation.

According to another embodiment of the present invention said proper energy consumption storage unit stores the proper energy consumption in the form of proper energy consumption selection table in which the factor related to fat deposition, an intensity in activity in life after pregnancy, and the term elapsed after pregnancy are listed in corresponding relation.

According to further embodiment of the present invention the factor related to fat deposition is any one of "BMI" before pregnancy, body weight before pregnancy, and body fat rate before pregnancy.

According to yet further embodiment of the present invention said fat deposition related factor acquisition unit includes an input key and/or an external data read-in terminal, said input key is operated by a user for entering the factor related to fat deposition.

According to yet further embodiment of the present invention said term-after-pregnancy acquisition unit includes: an input key; a clock unit; and a term-after-pregnancy calculation unit, wherein said input key is operated by the user for entering a date or expected date of delivery as well as the current date and time, said clock unit updates the current date and time depending on the entered current date and time, and said term-after-pregnancy calculation unit calculates the term elapsed after pregnancy depending on the entered date or expected date of delivery, the current date from the clock unit, and the pregnant period.

According to yet further embodiment of the present invention said number-of-activity step acquisition unit includes a detection unit, said detection unit produces a signal for indicating the number of activity steps in response to user's steps.

According to yet further embodiment of the present invention said activity energy consumption calculation unit includes: an input key; a clock unit; a calculation formula storage unit; and an arithmetic unit, wherein said input key is operated by the user for entering height or step width and body weight after pregnancy, said clock unit measures the time that has elapsed after the user started to walk, said calculation formula storage unit stores the calculation formula for calculating the activity energy consumption, and said arithmetic unit calculates the activity energy consumption, using the calculation formula for calculating the activity energy consumption stored in said calculation formula storage unit, depending on the entered height or step width and body weight after pregnancy, the number of activity steps acquired by the number-of-activity step acquisition unit, and the elapsed time that is measured by the clock unit.

According to yet further embodiment of the present invention said comparison and assessment unit includes: an calculation formula and advice table storage unit; an arithmetic unit; and a selection unit, wherein said calculation formula and advice table storage unit stores a calculation formula for calculating deficiency of energy consumption, a calculation formula for calculating deficiency of the number of activity steps, a calculation formula for calculating proper number of steps or a calculation formula for calculating rate of achievement, as well as an advice table, said arithmetic unit acts to calculate the deficiency of energy consumption using the calculation formula for calculating deficiency of energy consumption stored in the calculation formula and advice table storage unit, depending on the proper energy consumption selected from the proper energy consumption storage unit, and the activity energy consumption calculated by the arithmetic unit for activity energy consumption, to calculate the deficiency of the number of activity steps using the calculation formula for calculating deficiency of the number of activity steps stored in the calculation formula and advice table storage unit, depending on the calculated deficiency of energy consumption, to calculate proper number of steps using the calculation formula for calculating proper number of steps stored in the calculation formula and advice table storage unit, depending on the proper energy consumption selected from the proper energy consumption storage unit, or to calculate the rate of achievement using the calculation formula for calculating rate of achievement stored in the calculation formula and advice table storage unit, depending on the number of activity steps acquired by the number-of-activity step acquisition unit and the calculated proper number of steps, and said selection unit selects any one of advices in the advice table stored in the calculation formula and advice table storage unit, depending on the calculated rate of achievement.

According to yet further embodiment of the present invention said comparison and assessment result output unit includes a display unit, said display unit displays the result of comparison from the comparison and assessment unit.

BRIEF DESCRIPTION OF THE DRAWINGS

Now, the present invention will be described in more detail with reference to the accompanying drawings, in which.

DESCRIPTION OF THE PREFERRED EMBODIMENTS

Figure 1:
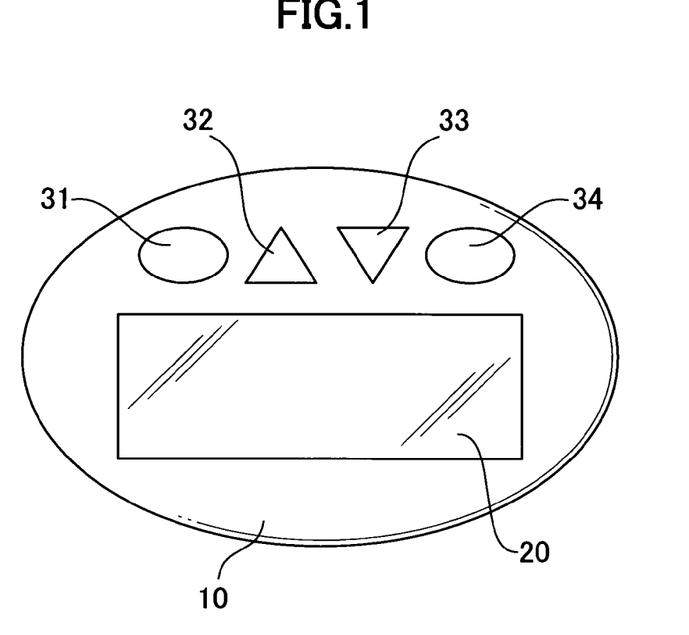
FIG. 1 is an external elevation view of a pedometer for use with a pregnant woman constructed according to one embodiment of the present invention.
Figure 2:
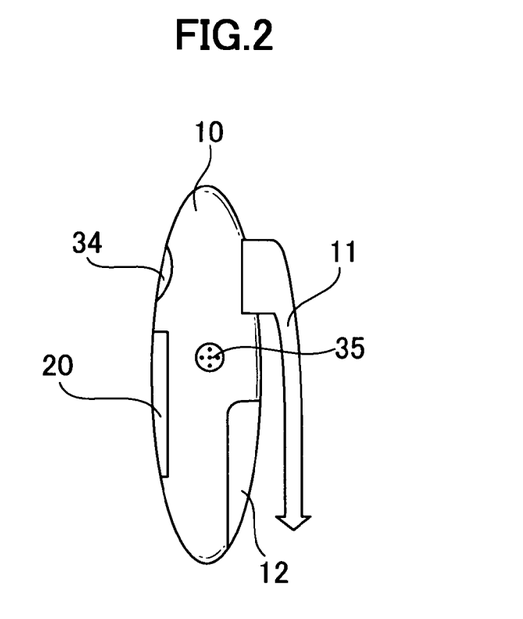
FIG. 2 is a side view of the pedometer for a pregnant woman in FIG. 1.

FIG. 1 is an external elevation view of a pedometer for use with a pregnant woman constructed according to one embodiment of the present invention. FIG. 2 is a side view of the pedometer for a pregnant woman in FIG. 1. Referring to FIGS. 1 and 2, the pedometer for a pregnant woman in this embodiment comprises a case 10 which includes, on the rear surface thereof, a clip 11 for attaching to e.g. a waist band of a user, and a lid 12 for a battery container. The case 10 further includes, on the front surface thereof, a display unit 20 made up of e.g. an LCD element, a setting button 31, an upward button 32, a downward button 33, and a display switching button 34. Furthermore, the case 10 includes an external data read-in terminal 35 positioned on the side surface thereof. The setting button 31, the upward button 32, the downward button 33, the display switching button 34, and the external data read-in terminal 35 together form an input section 30. The external data read-in terminal 35 is connected to a personal computer, a weight meter, a body fat meter, etc. for reading-in the relevant data.

Although not seen in FIGS. 1 and 2, the pedometer for a pregnant woman in this embodiment further includes a power supply 40 (FIG. 3) made up of a battery inserted into the battery container that is opened or closed by the lid 12 of the case 10, a detector section 50 (FIG. 3) formed of prior art pendulum type sensor positioned in the case 10 for detecting a step taken by a pregnant woman, an audio section 60 (FIG. 3) formed of a buzzer, etc., a oscillator section 70 (FIG. 3) formed of a vibrator, etc., and a microcomputer 80 (FIG. 3) for providing functions of an arithmetic unit, a controller unit, a storage unit and a clock unit.

Figure 3:
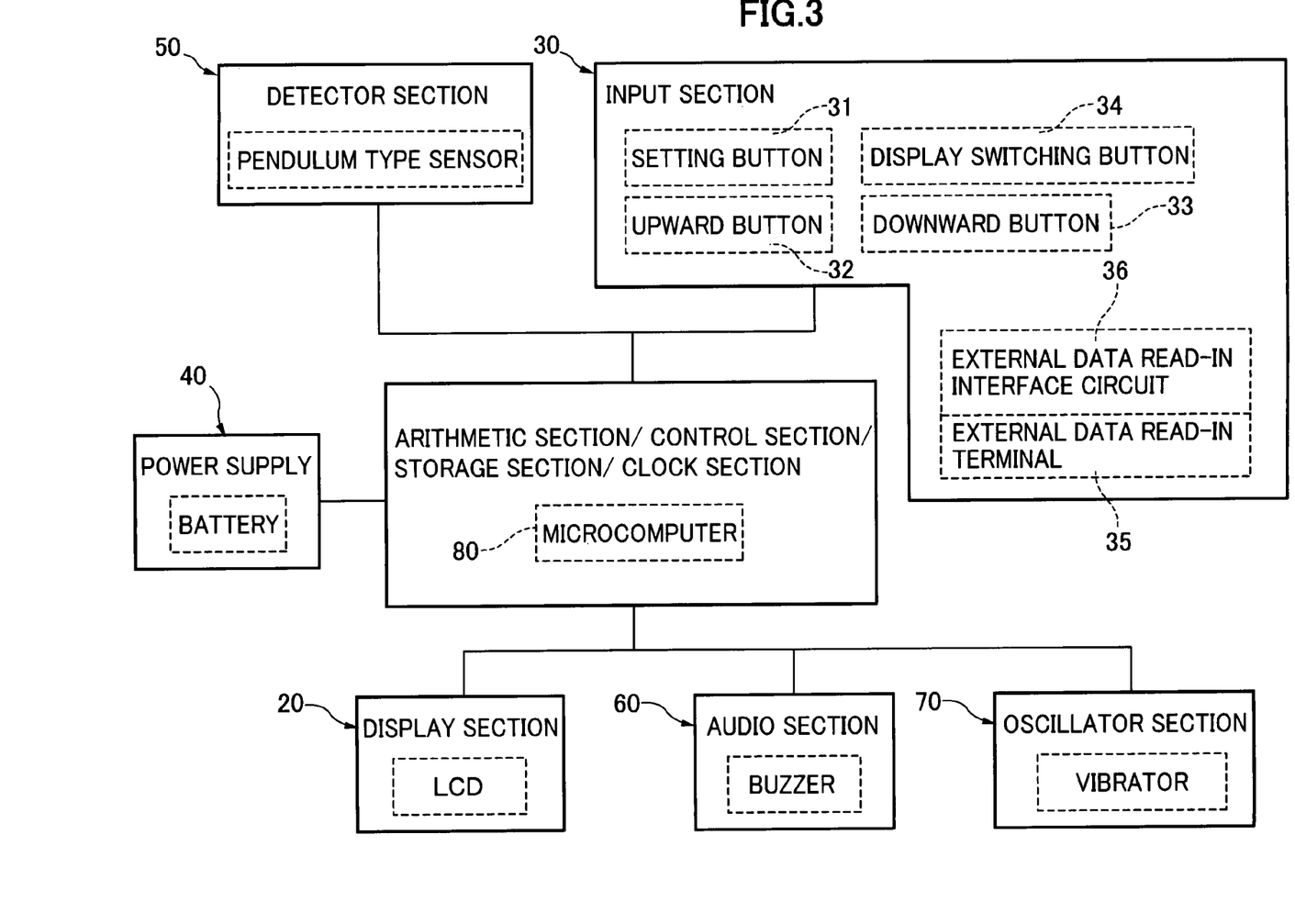
FIG. 3 is a block diagram illustrating electrical connection between components of the pedometer for a pregnant woman in FIG. 1.

FIG. 3 is a block diagram illustrating electrical connection between components of the pedometer for a pregnant woman, as described above with reference to FIG. 1. Referring to FIG. 3, the microcomputer 80 is powered by the power supply 40 to control the operation of the display section 20, the input section 30, the detector section 50, the audio section 60 and the oscillator section 70. The data from some external device connected to the external data read-in terminal 35 is transmitted to the storage section through an external data read-in interface circuit 36 under the control of the microcomputer 80. In the same manner, the input data from the setting button 31, the upward button 32, the downward button 33 and the display switching button 34 all together forming the input section 30 is transmitted to the storage section under the control of the microcomputer 80.

The input section 30 is provided for entering the data including date or expected date of delivery of a user, height, body weight before and after pregnancy, intensity in activity in life after pregnancy, body fat rate before and after pregnancy, current date and time, age, etc. The detector section 50 is provided for producing the walking data (or the number of activity steps) of the user.

The clock section which is one of the functions provided by the microcomputer 80 updates the current date and time depending on the data (current date and time) sent from the input section 30. After initial setting as described later, it also measures the period of time elapsed since measuring of the number of activity steps is started.

Figure 4:
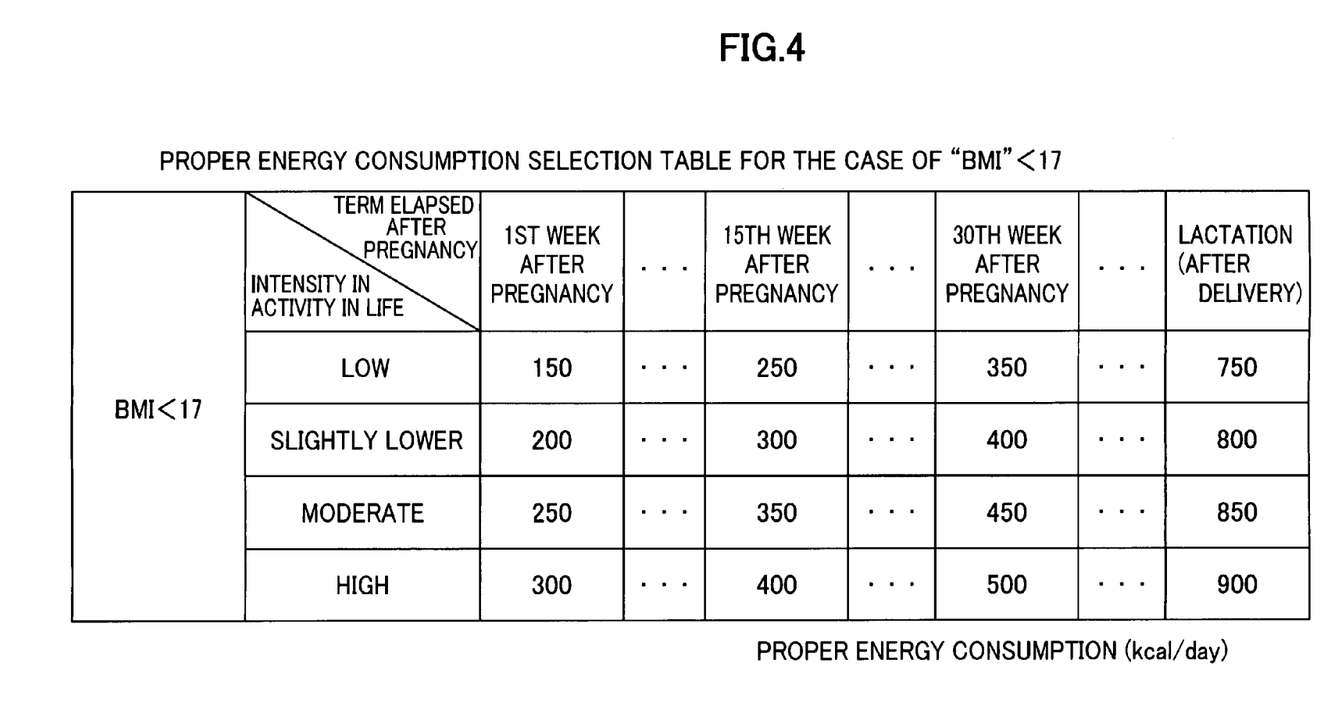
FIG. 4 is one example of a proper energy consumption selection table stored in a storage section of the pedometer for a pregnant woman in FIG. 1.
Figure 5:
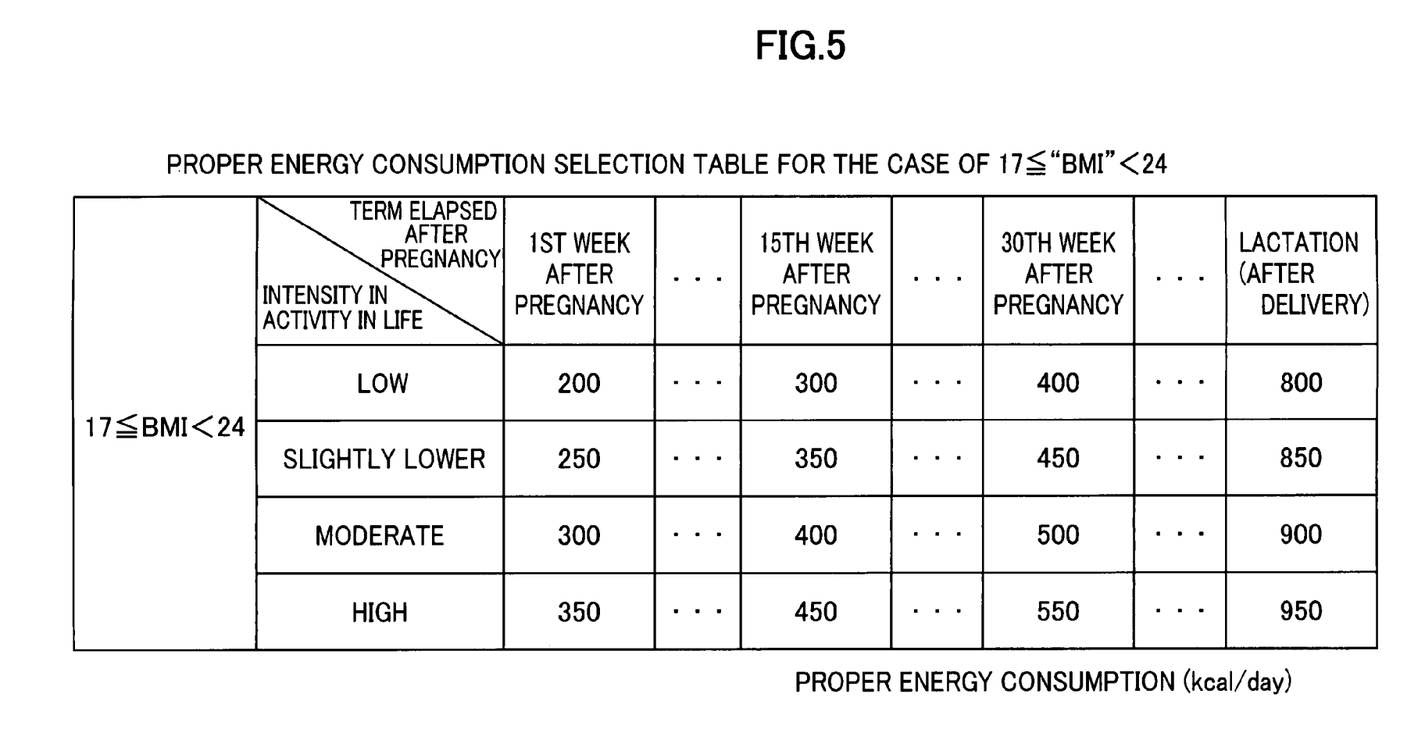
FIG. 5 is another example of a proper energy consumption selection table stored in the storage section of the pedometer for a pregnant woman in FIG. 1.
Figure 6:
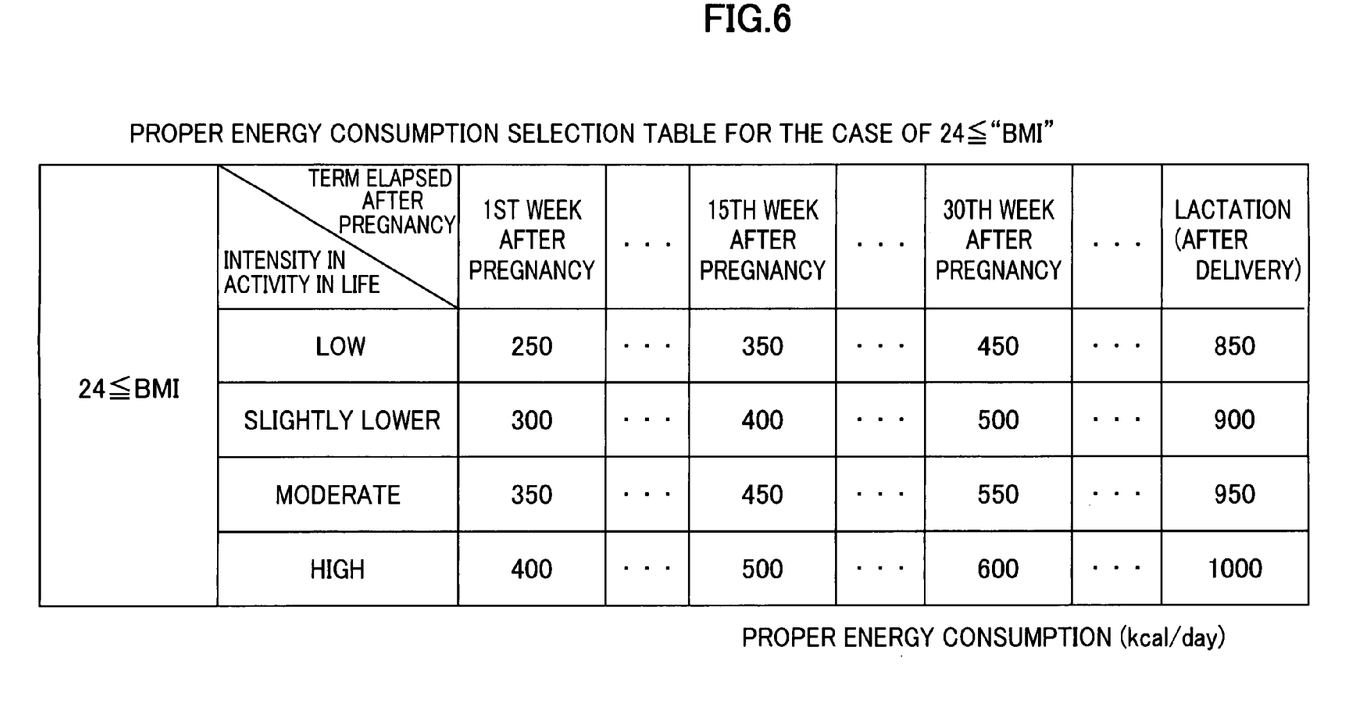
FIG. 6 is further example of a proper energy consumption selection table stored in the storage section of the pedometer for a pregnant woman in FIG. 1.
Figure 7:
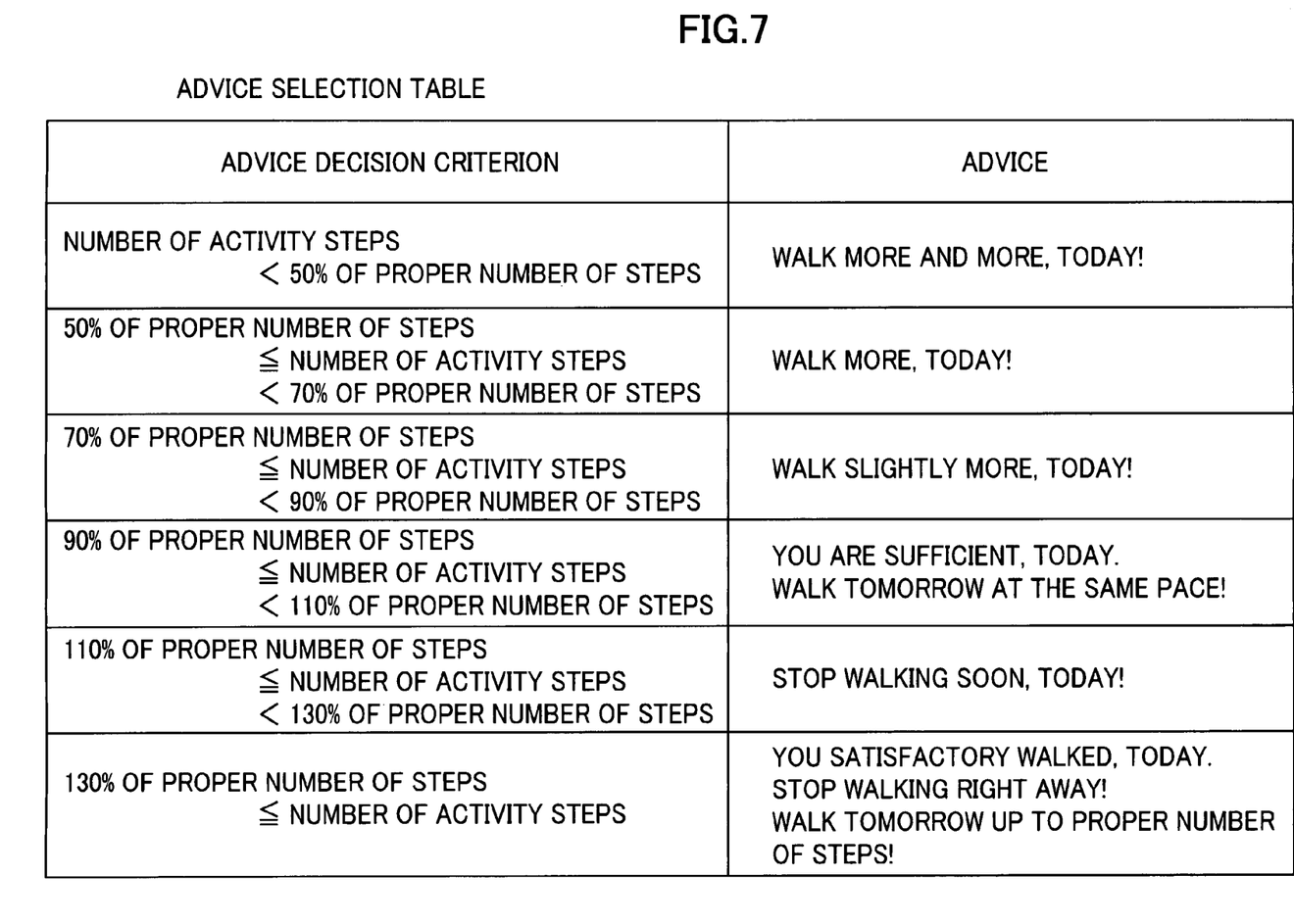
FIG. 7 is one example of an advice selection table stored in the storage section of the pedometer for a pregnant woman in FIG. 1.

The storage section which is another one of the functions provided by the microcomputer 80 stores the data listed in proper energy consumption selection table (which lists the proper energy consumption in the form of corresponding relation between "BMI" before pregnancy, intensity in activity in life after pregnancy, and term elapsed after pregnancy), as exemplified in FIGS. 4 to 6, the data listed in advice selection table (which lists advice messages in the form of corresponding relation between proper number of steps and number of activity steps), as exemplified in FIG. 7, and the following calculation formulae:

$$\text{Body Mass Index ``}BMI\text{'' before Pregnancy} = \text{Body Weight before Pregnancy ``}Wb\text{''} \div (\text{Height ``}H\text{''})^2 \quad (1)$$

$$\text{Step Width ``}S\text{''} = \text{Coefficient ``}k2\text{''} \times \text{Height ``}H\text{''} \quad (2)$$

$$\begin{aligned}\text{Activity Energy Consumption ``}Ea\text{''} &= \text{Coefficient ``}k1\text{''} \times \text{Body Weight after Pregnancy ``}W\text{''} \\ &\times (\text{Step Width ``}S\text{''} \times \text{Number of Activity Steps ``}Ca\text{''} \div \text{Elapsed Time ``}T\text{''})^2\end{aligned} \quad (3)$$

$$\text{Deficiency of Energy Consumption ``}Ef\text{''} = \text{Proper Energy Consumption ``}Er\text{''} - \text{Activity Energy Consumption ``}Ea\text{''} \quad (4)$$

$$\text{Deficiency of Number of Activity Steps ''}Cf'' = \sqrt{\frac{\text{DeficiencyofEnergyConsumption'' }Ef'' \times (\text{ElapsedTime'' }T'')^2}{\text{Coeficient'' }k1'' \times \text{BodyWeightafterPregenancy'' }W'' \times (\text{StepWidth'' }S'')^2}} \quad (5)$$

$$\text{Proper Number of Steps ''}Cr'' = \sqrt{\frac{\text{ProperEnergyConsumption'' }Er'' \times (\text{ElapsedTime'' }T'')^2}{\text{Coeficient'' }k1'' \times \text{BodyWeightafterPregnancy'' }W'' \times (\text{StepWidth'' }S'')^2}} \quad (6)$$

$$\text{Rate of Achievement} = \text{Number of Activity Steps ``}Ca\text{''} \div \text{Proper Number of Steps ``}Cr\text{''} \times 100 \quad (7)$$

The arithmetic section which is further one of the functions provided by the microcomputer 80 performs the following calculations and advice selection to provide the information characterizing the pregnant woman:

A first calculation is performed in the arithmetic section in such manner that the data of body weight and height before pregnancy, as entered via the input section 30, is substituted for the formula (1) for calculating Body Mass Index "BMI" before pregnancy, which formula is stored in the storage section, to produce the calculated "BMI" before pregnancy. Then, the term that has elapsed after pregnancy (i.e., how many weeks have been elapsed after pregnancy? or is it lactation period?) is calculated based on the data (date or expected date of delivery) entered via the input section 30, the data (current date) from the dock section, and the pregnant period (265 days from fertilization to delivery). Thereafter, the relevant proper energy consumption is selected from among the data in the proper energy consumption selection tables in FIGS. 4 to 6, which tables are stored in the storage section, based on the calculated "BMI" before pregnancy and the calculated term elapsed after pregnancy as well as the data (intensity in activity in life after pregnancy) entered via the input section 30. For example, if "BMI" before pregnancy is 20, the intensity in activity in life after pregnancy is moderate, and the term elapsed after pregnancy is 15$^{th}$ week, then the proper energy consumption of 400 kcal/day is selected.

A second calculation is performed in the arithmetic section in such manner that the data of height, as entered via the input section 30, is substituted for the formula (2) for calculating step width, which formula is stored in the storage section, to produce the calculated step width. Then, the calculated step width, the data of body weight after pregnancy entered via the input section 30, the walking data (number of activity steps) from the detection section 50, and the data (the time elapsed after measurement of the number of activity steps is started) from the clock section are substituted for the formula (3) for calculating activity energy consumption, which formula is stored in the storage section, to produce the calculated activity energy consumption.

A third calculation is performed in the arithmetic section in such manner that the selected proper energy consumption and the calculated activity energy consumption are substituted for the formula (4) for calculating deficiency of energy consumption, which formula is stored in the storage section, to produce the calculated deficiency of energy consumption. Thereafter, the calculated deficiency of energy consumption, the calculated step width, the data (body weight after pregnancy) entered via the input section 30, and the data (the time elapsed after measurement of the number of activity steps is started) from the clock section are substituted for the formula (5) for calculating deficiency of number of activity steps, which formula is stored in the storage section, to produce the calculated deficiency of number of activity steps.

A fourth calculation is performed in the arithmetic section in such manner that the selected proper energy consumption, the calculated step width, the data (body weight after pregnancy) entered via the input section 30, and the data (the time elapsed after measurement of the number of activity steps is started) from the clock section are substituted for the formula (6) for calculating proper number of steps, which formula is stored in the storage section, to produce the calculated proper number of steps.

A fifth calculation is performed in the arithmetic section in such manner that the number of activity steps from the detection section 50 and the calculated proper number of steps are substituted for the formula (7) for calculating rate of achievement, which formula is stored in the storage section, to produce the calculated rate of achievement. Then, an advice message is selected from among the advice selection table in FIG. 7, which is stored in the storage section.

Now, an entire operation of the pedometer for a pregnant woman according to the embodiment of the present invention will be described in more detail with reference to a main routine flow chart in FIG. 8 and a subroutine flow chart in FIG. 9.

Figure 8:
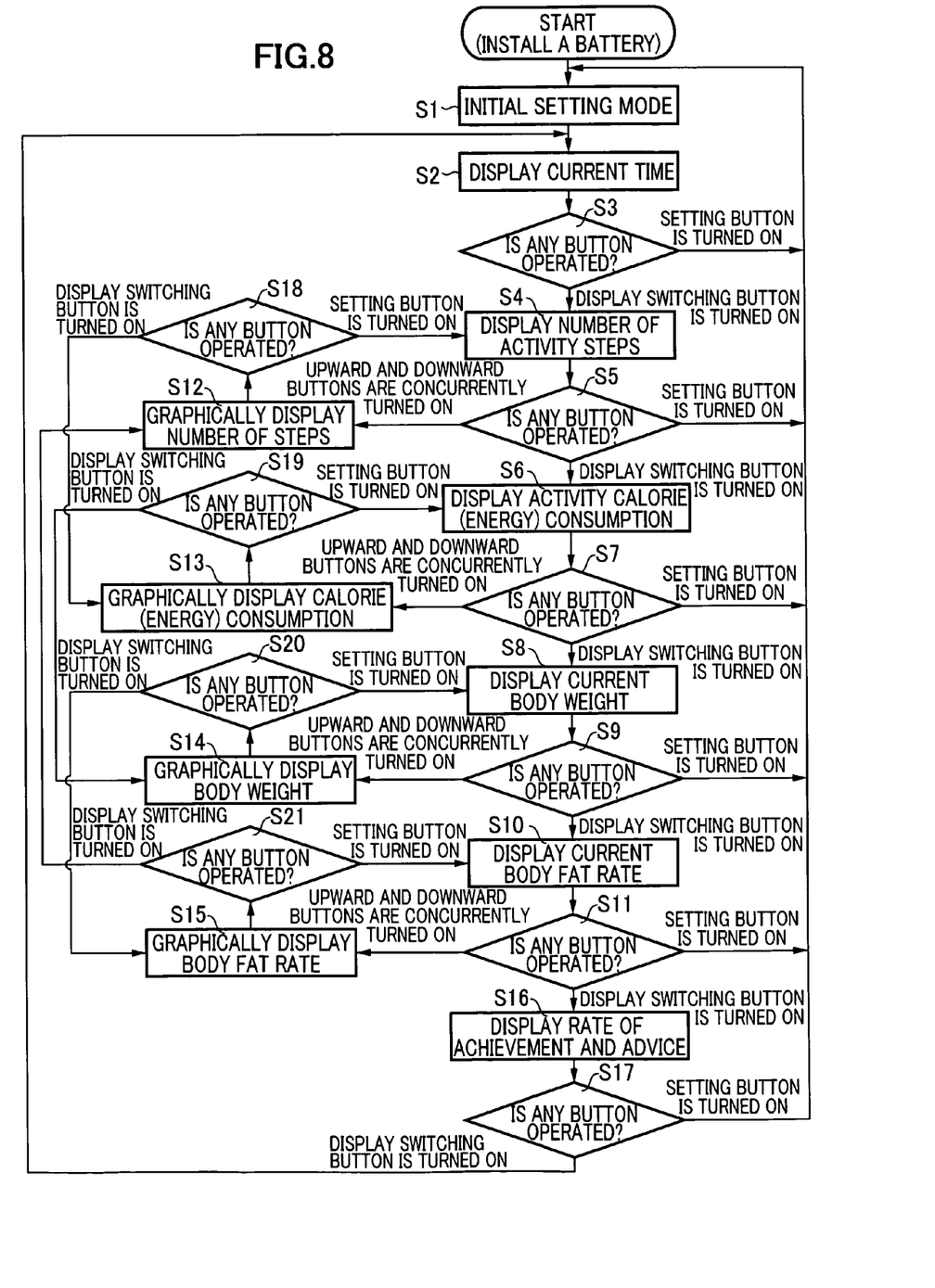
FIG. 8 is a main flow chart for explaining operation of the pedometer for a pregnant woman in FIG. 1.

Referring to the flow chart in FIG. 8, at "start" step, the lid 12 of the case 10 is removed and a battery is inserted into the battery container in the case 10. Then, the routine proceeds to "Initial Setting Mode" (step S1) where setting of characteristic data for a person under test (a pregnant woman, a pregnant woman in delivery room or a woman in lactation period) is performed. The initial setting mode at step S1 will be described with reference to the subroutine flow chart in FIG. 9.

Figure 9:
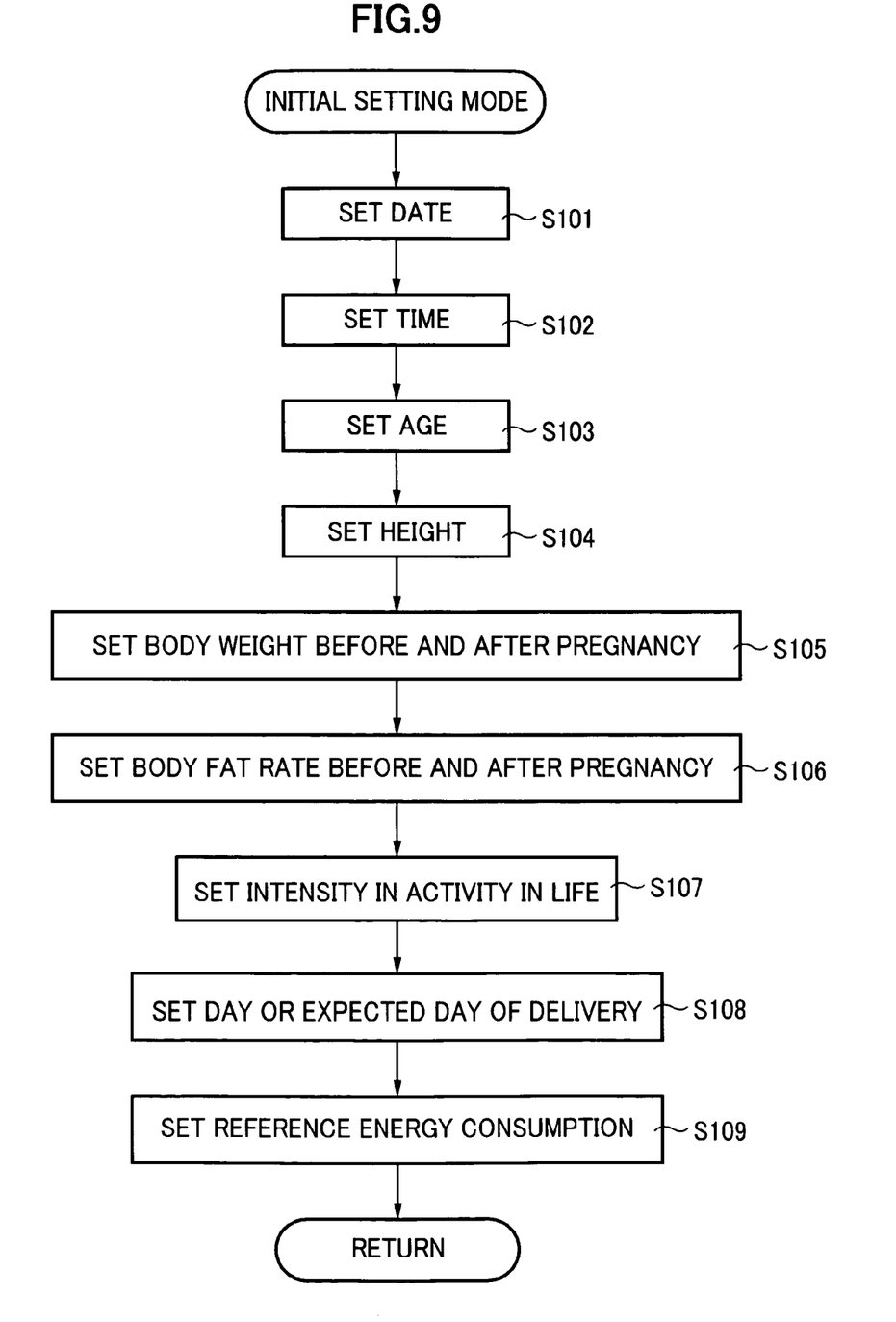
FIG. 9 is a subroutine flow chart for explaining operation of the pedometer for a pregnant woman in FIG. 1.

Referring to the subroutine flow chart in FIG. 9 illustrating the initial setting mode at step S1, first of all, at step S101, a date setting screen is displayed on the display section 20. Then, a cursor is moved to the desired position using the upward button 32 or the downward button 33 to set the numerical value with the display switching button 34 and to complete the setting with the setting button 31. Then, the routine sequentially proceeds to the subsequent setting steps including: time setting step S102; age setting step S103; height setting step S104; body weight before and after pregnancy setting step S105; body fat rate before and after pregnancy setting step S106; intensity in activity in life setting step S107; date or expected date of delivery setting step S108; and reference energy consumption setting step S109, where the setting is carried out in the same manner.

In particular, at the reference energy consumption setting step S109, said first calculation is performed in the arithmetic section on the basis of the data entered in each of the setting steps to display the selected proper energy consumption on the display section 20 as the reference energy consumption. Generally, the proper energy consumption is used as the reference energy consumption without any modification, but it may freely be modified by the user or the person under test, if necessary.

After completion of the reference energy consumption setting step S109 reading-in (or measurement) of the waling data (number of activity steps) via the detection section 50 is started and each of process steps as described above is performed in the arithmetic section. Then, the routine returns to the main routine flow chart in FIG. 8. At step S2 the current time is displayed on the display section 20 depending on the time entered via the input section 30 and the time counted by the clock section. When the number of activity steps reaches the proper number of steps after reading-in of the walking data is started then the audio section (i.e. a buzzer) sounds and the oscillator section (i.e. a vibrator) oscillates.

While the current time is displayed, if the setting button 31 is turned ON at step S3, the routine returns to the initial setting mode at step S1 where the data that has been set at each of the setting steps S101 to S109 can be modified. On the other hand, if the display switching button 34 is turned ON at step S3 the number of activity steps as measured by the detention section 50 is displayed on the display section 20 at step S4.

In the same manner, while the number of activity steps is displayed at step S4, if the display switching button 34 is turned ON at step S5, the activity energy consumption (calorie) calculated by the third calculation in the arithmetic section is displayed on the display section 20. While the activity calorie consumption is displayed, if the display switching button 34 is turned ON at step S7, the body weight after pregnancy (i.e. current body weight) entered via the input section 30 is displayed on the display section 20 at step S8. While the body weight after pregnancy is displayed, if the display switching button 34 is turned ON at step S9, the body fat rate after pregnancy (i.e. current body fat rate) entered via the input section 30 is displayed on the display section 20 at step S10. While the number of activity steps (at step S4), the activity calorie consumption (at step S6), the body weight after pregnancy (at step S8) or the body fat rate after pregnancy (at step S10) is displayed, if the upward button 32 and the downward button 33 are concurrently turned ON at step S5, S7, S9 or S11, respectively, then a previous historical data at each step is graphically displayed on the display section 20 at step S12, S13, S14 or S15. In particular, the number of steps is graphically displayed at step S12, the calorie consumption is graphically displayed at step S13, the body weight is graphically displayed at step S14, and the body fat rate is graphically displayed at step S15.

Figure 10:
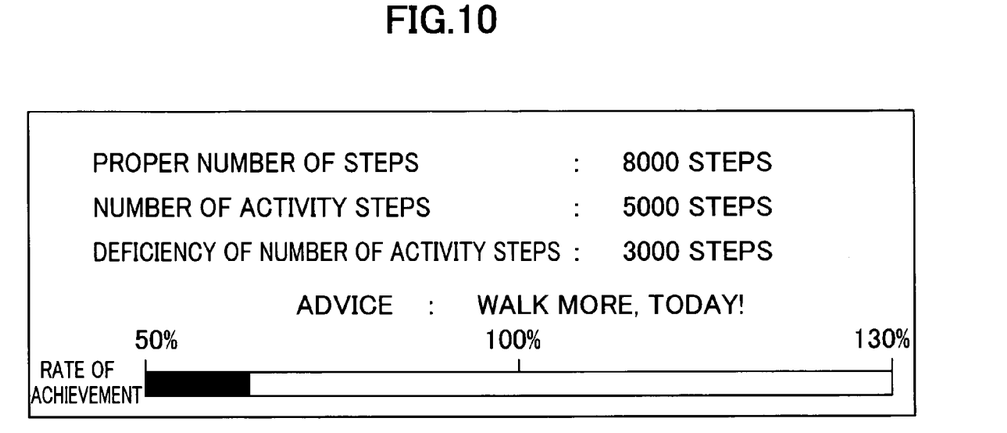
FIG. 10 is one example of an advice displayed on a display section of the pedometer for a pregnant woman in FIG. 1.

While the body fat rate after pregnancy is displayed at step S10, if the display switching button 34 is turned ON at step S11, then the rate of achievement for the number of activity steps and an advice message associated therewith, as shown in FIG. 10, are displayed on the display section 20 at step S16. In particular, the display in FIG. 10 includes: the number of activity steps, as measured by the detector section 50; the deficiency of number of activity steps, as calculated by the third calculation in the arithmetic section; the proper number of steps, as calculated by the fourth calculation in the arithmetic section; and the rate of achievement, as calculated by the fifth calculation in the arithmetic section, and the selected advice message.

While the rate of achievement for the number of activity steps and the advice message associated therewith are displayed at step S16, if the setting button 31 is turned ON at step S17, then the routine returns to the initial setting mode at step S1 where the data that has been set at each of the setting steps can be modified. On the other hand, if the display switching button 34 is turned ON at step S17 then the routine returns to step S2 where the current time is displayed on the display section 20.

In this embodiment, while the number of steps is graphically displayed at step S12, if the setting button 31 is turned ON at step S18, then the routine proceeds to step S4 where the number of activity steps is displayed. But, if the display switching button 34 is turned ON at that time then the routine proceeds to step S13 where the calorie consumption is graphically displayed. While the calorie consumption is graphically displayed at step S13, if the setting button 31 is turned ON at step S19, then the routine proceeds to step S6 where the activity calorie consumption is displayed. But, if the display switching button 34 is turned ON at that time then the routine proceeds to step S14 where the body weight is graphically displayed. While the body weight is graphically displayed at step S14, if the setting button 31 is turned ON at step S20, then the routine proceeds to step S8 where the current body weight is displayed. But, if the display switching button 34 is turned ON at that time then the routine proceeds to step S15 where the body fat rate is graphically displayed. While the body fat rate is graphically displayed at step S15, if the setting button 31 is turned ON at step S21, then the routine proceeds to step S10 where the current body fat rate is displayed. But, if the display switching button 34 is turned ON at that time then the routine proceeds to step S12 where the number of steps is graphically displayed.

If the setting button 31 is turned ON at each of steps S3, S5, S7, S9 and S11 then the routine enters the initial setting mode at step S1 where the data that has been set at each of the setting steps can be modified.

Although one embodiment of the present invention has been described above, the present invention is not necessarily limited to such embodiment. Instead, the present invention may be embodied in many other forms.

For example, the "BMI" before pregnancy listed in the proper energy consumption selection tables in FIGS. 4 to 6 may be replaced with body fat rate before pregnancy or other factors regarding the fat deposition. It is noted that the proper energy consumption selection tables in FIGS. 4 to 6 are prepared for the purpose of attaining the optimized fat deposition for mother's body in view of prevention of adiposity in pregnant period and of maintenance of good health in pregnant period.

Furthermore, it is possible that the intensity in activity in life after pregnancy is omitted from the proper energy consumption selection tables in FIGS. 4 to 6 so that the proper energy consumption is represented only in the form of corresponding relation between "BMI" before pregnancy and the term elapsed after pregnancy.

Moreover, "BMI" before pregnancy has been described as being calculated by substituting the body weight before pregnancy and the height for the formula (1) in the above embodiment. However, it may directly be entered via the input section 30.

It is apparent from the foregoing that a pedometer for use with a pregnant woman according to the present invention is configured to display proper number of steps, number of activity steps, deficiency of number of activity steps, rate of achievement, advice message, etc. on a display section if it is used with a pregnant woman or a woman in the predetermined interval after delivery. Therefore, walking activity can be taken according to the displayed data to attain proper calorie consumption, which realizes proper and easy control of calorie intake and calorie consumption in view of both body weight increase (body fat deposition) during pregnant period and health care.

What is claimed is:

1. A pedometer for use with a pregnant woman, comprising:
   a number-of-activity step acquisition unit;
   an activity energy consumption calculation unit;
   a proper energy consumption storage unit;
   a comparison and assessment unit; and
   a comparison and assessment result output unit, wherein
   said number-of-activity step acquisition unit acquires the number of activity steps taken by the pregnant woman,
   said activity energy consumption calculation unit calculates activity energy consumption based on said number of activity steps acquired,
   said proper energy consumption storage unit stores a proper energy consumption for the pregnant woman,
   said comparison and assessment unit compares the activity energy consumption calculated by said activity energy consumption calculation unit with the corresponding proper energy consumption stored in said proper energy consumption storage unit for assessing the activity energy consumption, and
   said comparison and assessment result output unit outputs the result of comparison and assessment for the activity energy consumption made by said comparison and assessment unit;
   further comprising a fat deposition related factor acquisition unit for acquiring a factor related to fat deposition of the pregnant woman, and a term-after-pregnancy acquisition unit for acquiring a term that has elapsed after pregnancy,
   in which said proper energy consumption storage unit stores the proper energy consumption in the form of a proper energy consumption selection table in which the factor related to fat deposition and the term elapsed after pregnancy are listed in corresponding relation.

2. A pedometer for use with a pregnant woman according to claim 1 in which the factor related to fat deposition is any one of "BMI" before pregnancy, body weight before pregnancy, and body fat rate before pregnancy.

3. A pedometer for use with a pregnant woman according to claim 2 in which said fat deposition related factor acquisition unit includes an input key and/or an external data read-in terminal, said input key is operated by a user for entering the factor related to fat deposition.

4. A pedometer for use with a pregnant woman according to claim 3 in which said term-after-pregnancy acquisition unit includes:
   an input key;
   a clock unit; and
   a term-after-pregnancy calculation unit, wherein
   said input key is operated by the user for entering a date or expected date of delivery as well as the current date and time,
   said clock unit updates the current date and time depending on the entered current date and time, and
   said term-after-pregnancy calculation unit calculates the term that has elapsed after pregnancy, based on the entered date or expected date of delivery, the current date from the clock unit, and the pregnant period.

5. A pedometer for use with a pregnant woman according to claim 4 in which said number-of-activity step acquisition unit includes a detection unit, said detection unit produces a signal for indicating the number of activity steps in response to user's steps.

6. A pedometer for use with a pregnant woman according to claim 5 in which said activity energy consumption calculation unit includes:
   an input key;
   a clock unit;
   a calculation formula storage unit; and
   an arithmetic unit, wherein
   said input key is operated by the user for entering height or step width and body weight after pregnancy,
   said clock unit measures the time that has elapsed after the user started to walk,
   said calculation formula storage unit stores the calculation formula for calculating the activity energy consumption, and
   said arithmetic unit calculates the activity energy consumption, using the calculation formula for calculating the activity energy consumption stored in said calculation formula storage unit, depending on the entered height or step width and body weight after pregnancy, the number of activity steps acquired by the numberof-activity step acquisition unit, and the elapsed time that is measured by the clock unit.

7. A pedometer for use with a pregnant woman according to claim 6 in which said comparison and assessment unit includes:

a calculation formula and advice table storage unit;
an arithmetic unit; and
a selection unit, wherein
said calculation formula and advice table storage unit stores a calculation formula for calculating deficiency of energy consumption, a calculation formula for calculating deficiency of the number of activity steps, a calculation formula for calculating proper number of steps or a calculation formula for calculating rate of achievement, as well as an advice table,
said arithmetic unit acts to calculate the deficiency of energy consumption using the calculation formula for calculating deficiency of energy consumption stored in the calculation formula and advice table storage unit, depending on the proper energy consumption selected from the proper energy consumption storage unit, and the activity energy consumption calculated by the arithmetic unit for activity energy consumption, to calculate the deficiency of the number of activity steps using the calculation formula for calculating deficiency of the number of activity steps stored in the calculation formula and advice table storage unit, depending on the calculated deficiency of energy consumption, to calculate proper number of steps using the calculation formula for calculating proper number of steps stored in the calculation formula and advice table storage unit, depending on the proper energy consumption selected from the proper energy consumption storage unit, or to calculate the rate of achievement using the calculation formula for calculating rate of achievement stored in the calculation formula and advice table storage unit, depending on the number of activity steps acquired by the number-of-activity step acquisition unit and the calculated proper number of steps, and
said selection unit selects any one of advices in the advice table stored in the calculation formula and advice table storage unit, depending on the calculated rate of achievement.

8. A pedometer for use with a pregnant woman according to claim 7 in which said comparison and assessment result output unit includes a display unit, said display unit displays the result of comparison from the comparison and assessment unit.

9. A pedometer for use with a pregnant woman according to claim 1 in which said fat deposition related factor acquisition unit includes an input key and/or an external data read-in terminal, said input key is operated by a user for entering the factor related to fat deposition.

10. A pedometer for use with a pregnant woman according to claim 1 in which said term-after-pregnancy acquisition unit includes:

an input key;
a clock unit; and
a term-after-pregnancy calculation unit, wherein
said input key is operated by the user for entering a date or expected date of delivery as well as the current date and time,
said clock unit updates the current date and time depending on the entered current date and time, and
said term-after-pregnancy calculation unit calculates the term that has elapsed after pregnancy, based on the entered date or expected date of delivery, the current date from the clock unit, and the pregnant period.

11. A pedometer for use with a pregnant woman, comprising:

a number-of-activity step acquisition unit;
an activity energy consumption calculation unit;
a proper energy consumption storage unit;
a comparison and assessment unit; and
a comparison and assessment result output unit, wherein
said number-of-activity step acquisition unit acquires the number of activity steps taken by the pregnant woman,
said activity energy consumption calculation unit calculates activity energy consumption based on said number of activity steps acquired,
said proper energy consumption storage unit stores a proper energy consumption for the pregnant woman,
said comparison and assessment unit compares the activity energy consumption calculated by said activity energy consumption calculation unit with the corresponding proper energy consumption stored in said proper energy consumption storage unit for assessing the activity energy consumption, and
said comparison and assessment result output unit outputs the result of comparison and assessment for the activity energy consumption made by said comparison and assessment unit;
further comprising a fat deposition related factor acquisition unit for acquiring a factor related to fat deposition of the pregnant woman, and a term-after-pregnancy acquisition unit for acquiring a term that has elapsed after pregnancy,
in which said proper energy consumption storage unit stores the proper energy consumption in the form of a proper energy consumption selection table in which the factor related to fat deposition, an intensity in activity in life after pregnancy, and the term elapsed after pregnancy are listed in corresponding relation.

12. A pedometer for use with a pregnant woman according to claim 11 in which the factor related to fat deposition is any one of "BMI" before pregnancy, body weight before pregnancy, and body fat rate before pregnancy.

13. A pedometer for use with a pregnant woman according to claim 12 in which said fat deposition related factor acquisition unit includes an input key and/or an external data read-in terminal, said input key is operated by a user for entering the factor related to fat deposition.

14. A pedometer for use with a pregnant woman according to claim 13 in which said term-after-pregnancy acquisition unit includes:

an input key;
a clock unit; and
a term-after-pregnancy calculation unit, wherein
said input key is operated by the user for entering a date or expected date of delivery as well as the current date and time,
said clock unit updates the current date and time depending on the entered current date and time, and
said term-after-pregnancy calculation unit calculates the term that has elapsed after pregnancy, based on the entered date or expected date of delivery, the current date from the clock unit, and the pregnant period.

15. A pedometer for use with a pregnant woman according to claim 14 in which said number-of-activity step acquisition unit includes a detection unit, said detection unit produces a signal for indicating the number of activity steps in response to user's steps.

16. A pedometer for use with a pregnant woman according to claim 15 in which said activity energy consumption calculation unit includes:

an input key;

a clock unit;

a calculation formula storage unit; and an arithmetic unit, wherein said input key is operated by the user for entering height or step width and body weight after pregnancy, said clock unit measures the time that has elapsed after the user started to walk, said calculation formula storage unit stores the calculation formula for calculating the activity energy consumption, and said arithmetic unit calculates the activity energy consumption, using the calculation formula for calculating the activity energy consumption stored in said calculation formula storage unit, depending on the entered height or step width and body weight after pregnancy, the number of activity steps acquired by the number-of-activity step acquisition unit, and the elapsed time that is measured by the clock unit.

17. A pedometer for use with a pregnant woman according claim 16 in which said comparison and assessment unit includes:

a calculation formula and advice table storage unit;

an arithmetic unit; and a selection unit, wherein said calculation formula and advice table storage unit stores a calculation formula for calculating deficiency of energy consumption, a calculation formula for calculating deficiency of the number of activity steps, a calculation formula for calculating proper number of steps or a calculation formula for calculating rate of achievement, as well as an advice table, said arithmetic unit acts to calculate the deficiency of energy consumption using the calculation formula for calculating deficiency of energy consumption stored in the calculation formula and advice table storage unit, depending on the proper energy consumption selected from the proper energy consumption storage unit, and the activity energy consumption calculated by the arithmetic unit for activity energy consumption, to calculate the deficiency of the number of activity steps using the calculation formula for calculating deficiency of the number of activity steps stored in the calculation formula and advice table storage unit, depending on the calculated deficiency of energy consumption, to calculate proper number of steps using the calculation formula for calculating proper number of steps stored in the calculation formula and advice table storage unit, depending on the proper energy consumption selected from the proper energy consumption storage unit, or to calculate the rate of achievement using the calculation formula for calculating rate of achievement stored in the calculation formula and advice table storage unit, depending on the number of activity steps acquired by the number-of-activity step acquisition unit and the calculated proper number of steps, and said selection unit selects any one of advices in the advice table stored in the calculation formula and advice table storage unit, depending on the calculated rate of achievement.

18. A pedometer for use with a pregnant woman according to claim 17 in which said comparison and assessment result output unit includes a display unit, said display unit displays the result of comparison from the comparison and assessment unit.

19. A pedometer for use with a pregnant woman, comprising:

a number-of-activity step acquisition unit;

an activity energy consumption calculation unit;

a proper energy consumption storage unit;

a comparison and assessment unit; and a comparison and assessment result output unit, wherein said number-of-activity step acquisition unit acquires the number of activity steps taken by the pregnant woman, said activity energy consumption calculation unit calculates activity energy consumption based on said number of activity steps acquired, said proper energy consumption storage unit stores a proper energy consumption for the pregnant woman, said comparison and assessment unit compares the activity energy consumption calculated by said activity energy consumption calculation unit with the corresponding proper energy consumption stored in said proper energy consumption storage unit for assessing the activity energy consumption, said comparison and assessment result output unit outputs the result of comparison and assessment for the activity energy consumption made by said comparison and assessment unit; and said comparison and assessment unit includes a calculation formula and advice table storage unit; an arithmetic unit; and a selection unit, wherein said calculation formula and advice table storage unit stores a calculation formula for calculating deficiency of energy consumption, a calculation formula for calculating deficiency of the number of activity steps, a calculation formula for calculating proper number of steps or a calculation formula for calculating rate of achievement, as well as an advice table, said arithmetic unit acts to calculate the deficiency of energy consumption using the calculation formula for calculating deficiency of energy consumption stored in the calculation formula and advice table storage unit, depending on the proper energy consumption selected from the proper energy consumption storage unit, and the activity energy consumption calculated by the arithmetic unit for activity energy consumption, to calculate the deficiency of the number of activity steps using the calculation formula for calculating deficiency of the number of activity steps stored in the calculation formula and advice table storage unit, depending on the calculated deficiency of energy consumption, to calculate proper number of steps using the calculation formula for calculating proper number of steps stored in the calculation formula and advice table storage unit, depending on the proper energy consumption selected from the proper energy consumption storage unit, or to calculate the rate of achievement using the calculation formula for calculating rate of achievement stored in the calculation formula and advice table storage unit, depending on the number of activity steps acquired by the number-of-activity step acquisition unit and the calculated proper number of steps, and said selection unit selects any one of advices in the advice table stored in the calculation formula and advice table storage unit, depending on the calculated rate of achievement.

* * * * *

UNITED STATES PATENT AND TRADEMARK OFFICE
CERTIFICATE OF CORRECTION

PATENT NO. : 7,072,791 B2 Page 1 of 1
APPLICATION NO. : 10/874376
DATED : July 4, 2006
INVENTOR(S) : Shinichi Harima et al.

It is certified that error appears in the above-identified patent and that said Letters Patent is hereby corrected as shown below:

On the Title page, item [75]

"Inventors", change " Tokorozama " to -- Tokorozawa --

Signed and Sealed this

Fifth Day of December, 2006

JON W. DUDAS
*Director of the United States Patent and Trademark Office*